(12) United States Patent
Wang et al.

(10) Patent No.: US 9,579,148 B2
(45) Date of Patent: Feb. 28, 2017

(54) IRRIGATED ABLATION ELECTRODE HAVING RECESSED SURFACE PORTIONS

(75) Inventors: Huisun Wang, Maple Grove, MN (US); Jeremy Dando, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 2200 days.

(21) Appl. No.: 11/939,206

(22) Filed: Nov. 13, 2007

(65) Prior Publication Data
US 2009/0125017 A1 May 14, 2009

(51) Int. Cl.
*A61B 18/14* (2006.01)
*A61B 18/00* (2006.01)

(52) U.S. Cl.
CPC ...... *A61B 18/1492* (2013.01); *A61B 2018/00029* (2013.01); *A61B 2218/002* (2013.01)

(58) Field of Classification Search
CPC ...... A61B 18/1492; A61B 2018/00029; A61B 2218/002
USPC ...................................... 606/41, 45
See application file for complete search history.

(56) References Cited

U.S. PATENT DOCUMENTS

| | | |
|---|---|---|
| 5,056,517 A | 10/1991 | Fenici |
| 5,230,349 A | 7/1993 | Langberg |
| 5,334,193 A | 8/1994 | Nardella |
| 5,348,554 A | 9/1994 | Imran et al. |
| 5,423,811 A | 6/1995 | Imran et al. |
| 5,462,521 A | 10/1995 | Brucker et al. |
| 5,545,161 A | 8/1996 | Imran |
| 5,643,197 A | 7/1997 | Brucker et al. |
| 5,658,278 A | 8/1997 | Imran et al. |
| 5,697,927 A | 12/1997 | Imran et al. |
| 5,792,140 A | 8/1998 | Tu et al. |
| 5,843,152 A | 12/1998 | Tu et al. |
| 5,893,884 A | 4/1999 | Tu |
| 5,913,856 A | 6/1999 | Chia et al. |

(Continued)

FOREIGN PATENT DOCUMENTS

WO 2005/048858 A1 6/2005

OTHER PUBLICATIONS

Thomas, et al., A Comparison Of Open Irrigated And Non-Irrigated Tip Catheter Ablation for Pulmonary Vein Isolation, Europace 6:330-335 (2004).

(Continued)

*Primary Examiner* — Michael Peffley
*Assistant Examiner* — Samantha Good
(74) *Attorney, Agent, or Firm* — Dykema Gossett PLLC (57) ABSTRACT

The present invention relates to ablation electrode assemblies. The present invention further relates to an irrigated ablation electrode assembly that includes a recessed portion that can improve fluid flow around the irrigated ablation electrode. The electrode includes an outer body portion having an outer surface, and an inner cavity defined within the outer body portion. The electrode further includes at least one passageway for fluid flow from the inner cavity to the outer surface of the body of the electrode. The passageway further defines an outlet on the external surface of the electrode, therein allowing the fluid to flow on and/or around the electrode surface. The outer surface of the electrode further includes a recessed portion. The outlet of the passageway is disposed at least partially within the recessed portion. The fluid that exits the passageway may flow within the recessed portion to improve irrigation of the electrode.

18 Claims, 4 Drawing Sheets

(56) References Cited

U.S. PATENT DOCUMENTS

| | | | |
|---|---|---|---|
| 5,919,188 | A | 7/1999 | Shearon et al. |
| 6,015,407 | A | 1/2000 | Rieb et al. |
| 6,017,338 | A | 1/2000 | Brucker et al. |
| 6,120,476 | A | 9/2000 | Fung et al. |
| 6,171,275 | B1 | 1/2001 | Webster, Jr. |
| 6,217,576 | B1 | 4/2001 | Tu et al. |
| 6,602,242 | B1 | 8/2003 | Fung et al. |
| 6,611,699 | B2 | 8/2003 | Messing |
| 6,942,661 | B2 | 9/2005 | Swanson |
| 7,166,105 | B2 | 1/2007 | Mulier et al. |
| 2004/0054272 | A1 | 3/2004 | Messing |
| 2005/0177151 | A1 | 8/2005 | Coen et al. |
| 2007/0156131 | A1 | 7/2007 | Datta |

OTHER PUBLICATIONS

Wittkampf, et al., Radiofrequency Ablation with a Cooled Porous Electrode Catheter, JACC vol. 11, No. 2, Feb. 1988: 17A Abstracts.
Wittkampf, et al., Saline-Irrigated Radiofrequency Ablation Electrode with External Cooling, Journal of Cardiovascular Electrophysiology, vol. 16, No. 3, Mar. 2005.

IRRIGATED ABLATION ELECTRODE HAVING RECESSED SURFACE PORTIONS

BACKGROUND OF THE INVENTION a. Field of the Invention

The instant invention relates to ablation electrodes and/or electrode assemblies. The present invention further relates to ablation electrodes and/or assemblies having a mechanism for irrigating targeted areas. The present invention further relates to irrigated ablation electrodes and/or assemblies that include at least one recessed portion.

b. Background Art

Electrophysiology catheters have been used for an ever-growing number of procedures. For example, catheters have been used for diagnostic, therapeutic, and ablative procedures, to name just a few examples. Typically, a catheter is manipulated through the patient's vasculature and to the intended site, for example, a site within the patient's heart, and carries one or more electrodes, which may be used for ablation, diagnosis, or other treatments.

There are a number of methods used for ablation of desired areas, including for example, radiofrequency (RF) ablation. RF ablation is accomplished by transmission of radiofrequency energy to a desired target area through an electrode assembly to ablate tissue at the target site. Because RF ablation may generate significant heat, which if not controlled can result in excessive tissue damage, such as steam pop, tissue charring, and the like, it is desirable to include a mechanism to irrigate the target area and the device with biocompatible fluids, such as saline solution. The use of irrigated ablation catheters can also prevent the formation of soft thrombus and/or blood coagulation.

Typically, there are two classes of irrigated electrode catheters, open and closed irrigation catheters. Closed ablation catheters usually circulate a cooling fluid within the inner cavity of the electrode. Open ablation catheters typically deliver the cooling fluid through open outlets or openings on the surface of the electrode. Open ablation catheters use the inner cavity of the electrode, or distal member, as a manifold to distribute saline solution, or other irrigation fluids known to those skilled in the art, to one or more passageways that lead to openings/outlets provided on the surface of the electrode. The saline thus flows directly through the outlets of the passageways onto the distal electrode member. This direct flow of fluid through the distal electrode tip lowers the temperature of the distal tip during operation, rendering accurate monitoring and control of the ablative process more difficult. Accordingly, it is desirable to have a method that allows for cooling of the electrode while having accurate monitoring and control of the ablative process.

Overall, open flush irrigated ablation catheters may improve the safety of RF catheter ablation by preventing protein aggregation and blood coagulation. In addition, in order to improve and/or maximize the effect of irrigation, it is very important to maintain all irrigation holes open at any possible tissue contact orientations. During the performance of various procedures, some of the irrigation holes may be plugged when the holes are facing down to the tissue during the ablation procedure.

BRIEF SUMMARY OF THE INVENTION

The present invention relates to ablation electrode assemblies. The present invention further relates to an irrigated ablation electrode assembly that includes a recessed portion that maximizes fluid flow around the irrigated ablation electrode. It is desirable to have an irrigated ablation catheter which aids in preventing the openings/outlets of the fluid passageways (or irrigation holes) from being blocked and/or clogged when the holes are facing down to the tissue therein improving fluid flow about the ablation electrode.

The present invention relates to an electrode for an irrigated ablation catheter assembly. The electrode includes an outer body portion having an outer surface and an inner cavity defined within the outer body portion. The electrode further includes at least one passageway for fluid flow from the inner cavity to the outer surface of the body of the electrode. The passageway further defines an outlet on the external surface of the electrode allowing the fluid to flow on and/or around the electrode surface. The outer surface of the electrode further includes a recessed portion. The outlet of the passageway is disposed within the recessed portion. The fluid that exits out of the passageway flows within the recessed portion and can improve and/or maximize irrigation of the electrode.

The present invention further relates to an irrigated ablation electrode for use with an irrigated catheter assembly. The irrigated ablation electrode includes a proximal member having at least one passageway extending from an inner cavity and/or manifold to the external surface of the electrode to allow for the flow of fluid. The passageway provides an outlet disposed on an external surface of the proximal member of the electrode. The electrode further includes a distal member connected to or coupled with the proximal member, therein defining an external surface of the electrode. The distal member may further include an ablation member or ablative surface. In an embodiment, the electrode further includes a recessed portion disposed on the external surface of the electrode. The opening or outlet of the passageway is disposed within the recessed portion.

The present invention further relates to an ablation catheter system including an irrigated ablation electrode connected to a catheter shaft, therein forming an irrigated catheter assembly connected to an energy source and a fluid source.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant invention relates to irrigated ablation electrodes and electrode assemblies and to the use of the irrigated ablation electrodes and assemblies in connection with catheter assemblies. For purposes of this description, similar aspects among the various embodiments described herein will be referred to by the same reference number. As will be appreciated, however, the structure of the various aspects may be different among the various embodiments. The present embodiments describe RF ablation electrodes and assemblies, but it is contemplated that the present invention is equally applicable to any number of other ablation electrodes and assemblies where irrigation of the targeted tissue areas may be desirable.

Figure 1:
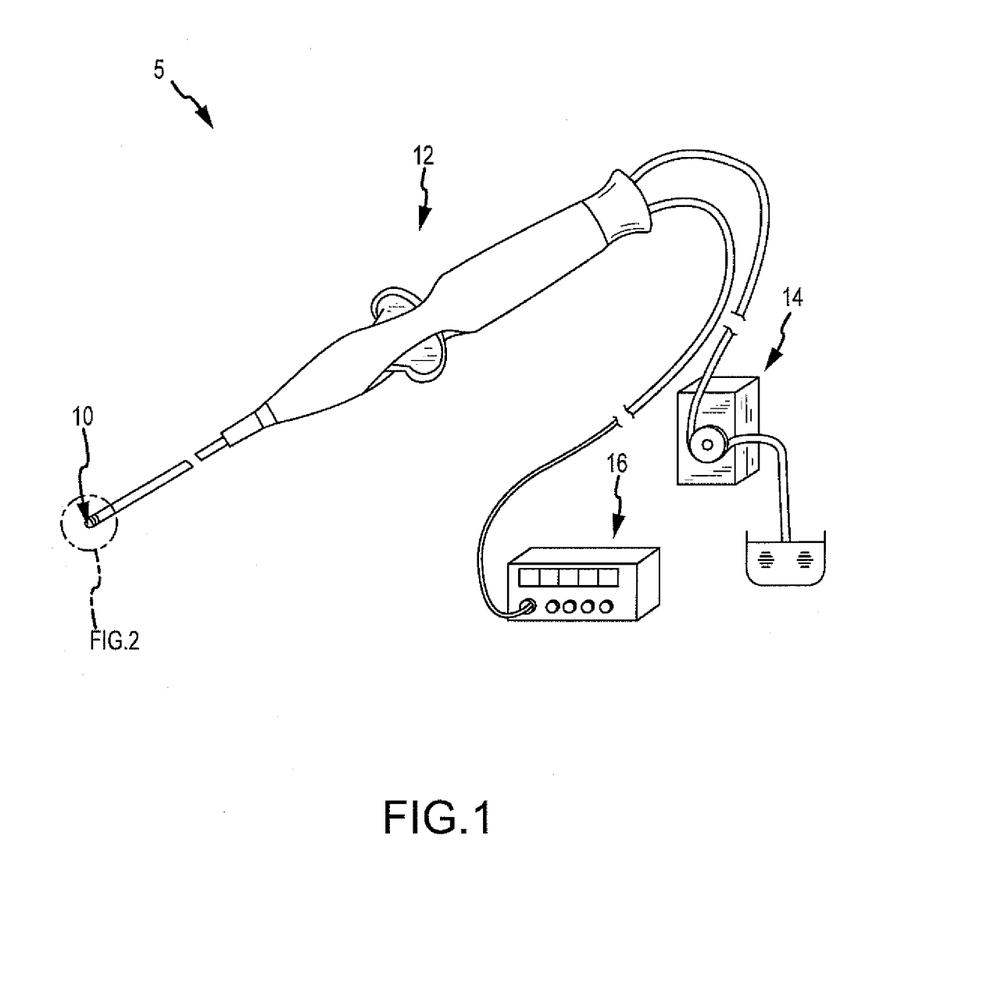
FIG. 1 is an isometric view of an ablation catheter system according to an embodiment of the present invention including an irrigated ablation electrode in conjunction with an irrigated catheter assembly operably connected to an energy source and a fluid source.

As seen in the embodiment illustrated in FIG. 1, the ablation electrode 10 may comprise part of an irrigated ablation catheter assembly 12 operably connected to a fluid source 14, such as a pump assembly, and an energy source 16, such as an RF generator assembly, therein comprising a catheter system 5. The fluid source and energy source may serve to facilitate the operation of ablation procedures and may involve monitoring any number of chosen variables (e.g., temperature of ablation electrode, ablation energy, and position of the assembly), assisting in manipulation of the assembly during the use, and providing the requisite energy source delivered to the electrode 10. Furthermore, additional components may be integrated into the system 5, such as visualization, mapping and navigation components known in the art, including among other things, NavX® or other systems. The present embodiments describe RF ablation electrodes and assemblies, but it is contemplated that the present invention is equally applicable to any number of other ablation electrodes and assemblies where the temperature of the device and the targeted tissue area may be factors during the procedure.

The general structural and functional features of catheter systems such as those generally comprising catheter assembly 12, fluid source 14 and energy source 16 are well-known to those of skill in the art. For example, the fluid source 14 can comprise various known assembly, including fixed volume rolling pumps, variable volume syringe pumps and other pump assembly known to those skill in the art. Moreover, the fluid provided by fluid source 14 may comprise a suitable biocompatible fluid, such as saline. The energy source 16 may comprise an IBI-1500T RF Cardiac Ablation Generator available from Irvine Biomedical, Inc. The energy source 16 can also comprise various other known energy sources. FIGS. 2-8B, discussed in more detail below, illustrate ablation electrodes 10 according to alternate embodiments of the present invention.

Figure 2:
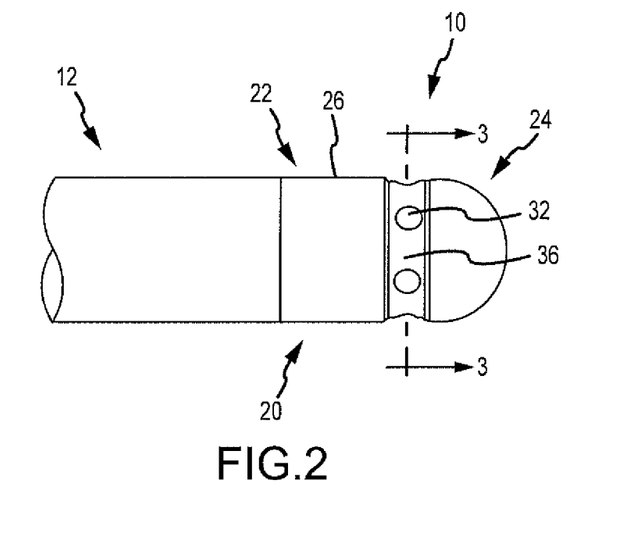
FIG. 2 is a side plan view of an irrigated ablation electrode connected to the catheter shaft in accordance with an embodiment of the present invention.

FIG. 2 is a plan view of an ablation electrode 10 connected to a catheter shaft as associated with catheter assembly 12. A fluid delivery conduit or tube (not shown) is connected to the catheter shaft to deliver saline or any other biocompatible liquid to the ablation electrode 10.

An exemplary embodiment of the ablation electrode 10, shown in FIG. 2, includes an outer body portion 20 having a proximal portion 22 and a distal portion 24. The outer body 20 of electrode 10 includes an outer surface 26. In an embodiment, the distal portion 24 of the electrode 10 may include an ablative surface for performing the ablation and transferring ablative energy to a tissue surface. The electrode 10 may be provided on the distal end of the catheter shaft 30, therein forming a catheter assembly 12. Alternate embodiments of electrode 10 may be provided wherein, body portion 20 of electrode 10 having proximal portion 22 and distal portion 24 may be formed by one unitary piece or may be formed by two or more separate pieces that are coupled in a number of methods known in the art to form electrode 10.

Figure 3:
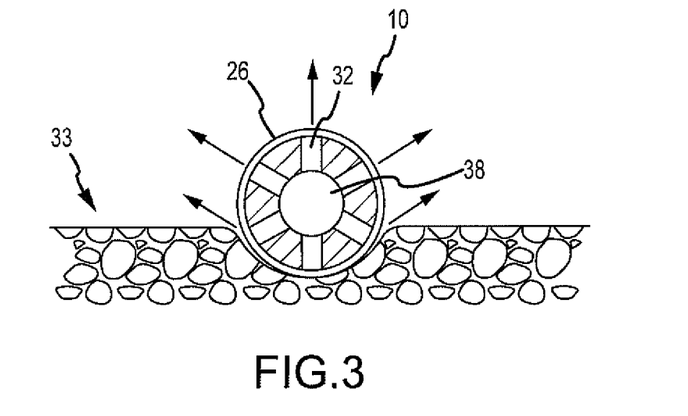
FIG. 3 is a cross sectional view of the embodiment of the irrigated electrode along lines 3-3 of FIG. 2 in contact with target tissue.

As further illustrated in FIGS. 2 and 3, an embodiment of electrode 10 may further include at least one fluid passageway 32 extending to outer surface 26 of electrode 10 therein providing an outlet or opening which allows for the flow of fluid from inner cavity 38 to outer surface 26 of electrode 10. Passageway may include and be referred to as conduit(s), irrigation port(s), irrigation hole(s), channel(s), or any other type of structure used by one of ordinary skill in the art. A number of fluid passageways 32 may be provided by electrode 10 in a number of configurations. As shown in FIG. 3, one embodiment of electrode 10 includes six fluid passageways 32. In accordance with alternate embodiments, the number of fluid passageways may vary depending on the configuration and use of the ablation electrode. Moreover, fluid passageways 32 may be disposed circumferentially about electrode 10 extending from inner cavity 38 to the outer circumference of electrode 10.

As shown in FIG. 2, in an embodiment, electrode 10 further provides a recessed portion 36. In accordance with one embodiment, recessed portion 36 may be disposed circumferentially about the outer surface 26 of electrode 10. The recessed portion may include various configurations, such as a groove or any other type of recessed area. Fluid passageways 32 extend from inner cavity 38 to outer surface 26 of electrode 10 and the outlet/opening of passageways 32 are disposed at least partially within recessed portion 36. In the configuration shown, the passageways 32 are disposed entirely within recessed portion 36. Recessed portion 36, as illustrated in FIG. 2, may be a groove having a substantially constant width and depth therein providing a uniform recessed portion 36 disposed around the circumference of electrode 10. The depth of the recessed portion 36 can be configured relative to the size of fluid passageway 32. For some embodiments, the width of the recessed portion 36 may be slightly larger or smaller than the diameter of fluid passageways 32, more particularly, the opening or outlet of passageways 32. In an embodiment, recessed portion 36 may have a uniform width of between 8-20 thousandths of an inch to correspond to the relative width of the fluid passageways 32. If the passageways 32 have variable widths with variable sized openings, the width of recessed portion 36 may correspond in size to the passageway and/or openings having the largest diameter. Moreover, in alternate embodiments, as discussed further below, the recessed portion may be provided having a variable width.

As previously mentioned, distal portion 24 of electrode 10 may further include an ablative surface that delivers ablative energy to a target tissue area. The distal portion 24 is generally comprised of any electrically, and potentially thermally, conductive material known to those of ordinary skill in the art. Examples of thermally conductive material include gold, platinum, iridium, palladium, stainless steel, and as well as various combinations thereof. Moreover, alternate designs of electrodes are contemplated by the present invention and may be integrated with the catheter assembly 12 of the present invention, such as tip electrodes, ring electrodes and any combinations thereof.

Proximal portion 22 of electrode 10 may be comprised of various materials, including electrically conductive material, such as that provided by distal portion 24 of the electrode assembly 10, reduced electrically and/or thermally conductive material, and/or an electrically nonconductive and/or thermally insulating material. Similarly, recessed portion 36 may be formed from a number of materials depending on the design of the electrode assembly.

FIG. 3 is a cross-sectional view of FIG. 2 taken along line 3-3, illustrating the flow of fluid from passageways 32 provided by one embodiment of irrigated ablation electrode 10. In particular, the outlets of passageways 32 within recessed portion 36 permit fluid to flow from passageways 32 even when electrode 10 is placed in contact with a target tissue area 33, for example, as shown in FIG. 3. Accordingly, tissue area 33 is in contact with outer surface 26 of electrode 10. Upon contact of the electrode 10 with tissue 33, recessed portion 36 provides a space between outer surface 26 and the opening/outlet of passageways 32 to allow for substantially uninterrupted or unimpeded flow of fluid from inner cavity 38 of electrode 10 through passageway 32. The space, for example, may correspond to the depth of recessed portion 36. The flow of fluid from passageways 32 into recessed portion 36 prevents the blocking and/or clogging of passageways 32. Moreover, the fluid may be cooled to aid in and/or achieve the cooling of the electrode during an ablation procedure.

Figure 4A:
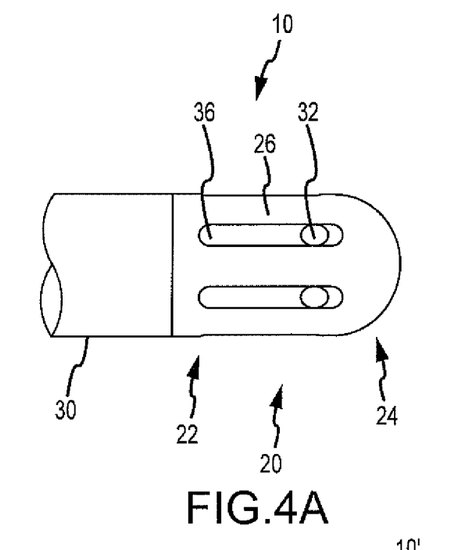
FIGS. 4A and 4B are plan views of alternate embodiments of an irrigated ablation electrode.
Figure 4B:
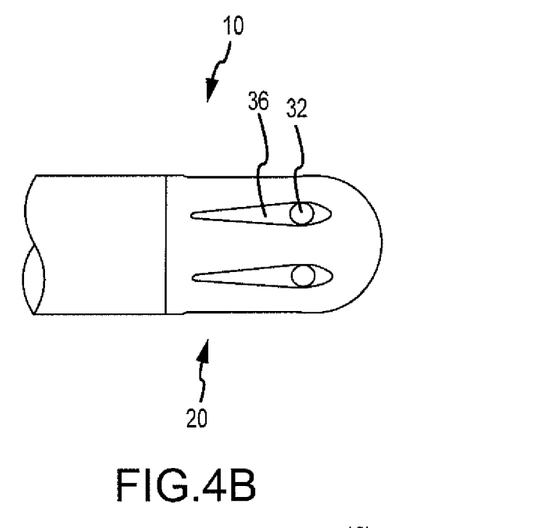
Figure 5A:
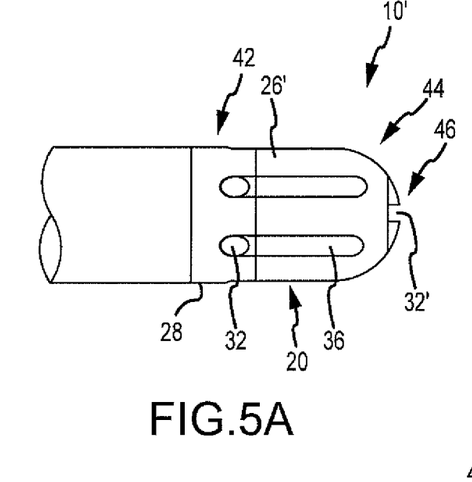
FIGS. 5A and 5B are plan views of alternate embodiments of an irrigated ablation electrode.
Figure 5B:
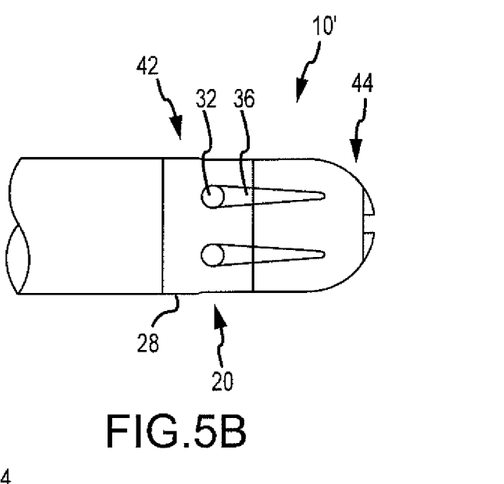

As can be seen in FIGS. 4A and 4B, as well as in FIGS. 5A and 5B, alternate embodiments of the present invention may incorporate the use of recessed portions on the outer surface 26 of an electrode 10, 10'. The electrodes 10 and 10' may have alternate configurations and/or a number of embodiments depending on the design of the electrodes.

In alternate embodiments, FIGS. 4A and 4B provide a conventional electrode 10 including an outer body portion 20 having an outer surface 26. Electrode 10 is generally cylindrical in shape with a hemispherical end. Electrode 10 includes a proximal portion 22 and a distal portion 24. Electrode 10 further includes at least one passageway 32 extending from an inner cavity to outer surface 26 having an opening to the passageway directed towards distal portion 24 of electrode 10. Although not shown, passageways 32 are generally in fluid contact with the inner cavity as previously discussed.

Passageways 32 may further be provided in various orientations within electrode 10. In an embodiment, passageways 32 may extend from an inner cavity to outer surface 26 substantially in a perpendicular direction, for example, forming a 90 degree angle with the central longitudinal axis (A) of electrode 10. In another embodiment, passageways 32 may extend from the inner cavity to outer surface 26 directed towards distal portion 24 of electrode 10, at an angle less than 90 degrees with respect to the central longitudinal axis (A). Moreover, in another embodiment, passageways 32 may extend from the inner cavity to outer surface 26 directed towards proximal portion 22 of electrode 10 at an angle greater than 90 degrees with the central longitudinal axis (A) (or less than 90 degrees when taken from the alternate direction). As a result, passageways 32 may provide openings/outlets in various orientations on the outer surface 26 of electrode 10. As seen in FIGS. 4A and 4B, passageways 32 provide outlets on distal portion 24 of the electrode 10. Embodiments of the present invention further provide for configurations having a plurality of recessed portions 36 on outer surface 26 of electrode 10.

An alternate embodiment of the ablation electrode 10, as shown in FIG. 4A, includes a separate or independent recessed portion 36 for each passageways 32. The recessed portions 36 extend along the longitudinal axis of body 20 and are circumferentially disposed about electrode 10. In general, the length of recessed portions 36 may vary depending on the length of electrode 10. In one embodiment, the length of recessed portions 36 is less than the length of electrode 10, therein providing sufficient surface on distal portion 24 of electrode 10 to ensure that sufficient contact can be made between the electrically conductive material of electrode 10 and/or the ablative surface provided by distal portion 24 with the target tissue to perform an ablative procedure.

FIG. 4A shows an embodiment wherein recessed portions 36 are provided with a substantially constant width (w). The substantially constant width corresponds to the diameter of passageway 32. In particular, the constant width corresponds to the diameter of the opening/outlet of passageway 32. An alternate embodiment, as shown in FIG. 4B, provides a plurality of recessed portions 36 on the electrode surface 26, wherein the width of one or more sections of recessed portions 36 may be variable. For example, the width of recessed portions 36 may taper as the portion, or groove, extends towards the proximal portion 22 of electrode 10. Although not shown, in an alternate embodiment the orientation can be reversed, such that the opening/outlets to passageways 32 are provided by proximal portion 22 of electrode 10 and recessed portions 36 extend towards distal portion 24 of electrode 10. Various alternative configurations of recessed portions 36 may further be provided based on the configuration of the ablation electrode 10, such as recessed portions 36 having constant or variable depths, alternate positioning of the passageways 32 or opening of passageways 32 within the recessed portions, and various combinations thereof. Furthermore, the embodiments illustrated in FIGS. 4A and 4B show a single passageway having an opening disposed in a single recessed grove 36. Although a one-to-one configuration may be provided, alternate embodiments having a number of passageway openings associated with one recessed portion are also contemplated by the present invention.

Figure 7:
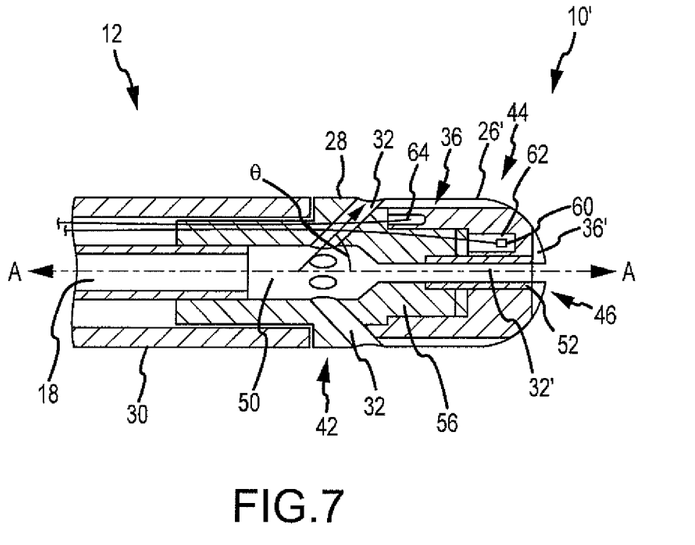
FIG. 7 is a cross-sectional view of the irrigated ablation electrode in an alternate embodiment as shown in FIG. 5A.

Alternate embodiments of the present invention are further provided in FIGS. 5A and 5B. Electrode 10' is provided having a proximal member 42 and a distal member 44. Proximal member 42 may be cylindrical in shape. Distal member 44 may be cylindrical in shape and includes a hemispherical end forming a distal end 46. In an embodiment, proximal member 42 and distal member 44 are two component parts that are coupled or connected together using techniques known in the art to form electrode 10' having an outer surface 26'. Accordingly, electrode 10' may be referred to as an electrode assembly. A plurality of fluid passageways 32 extend from an inner cavity or manifold 50 (as shown in FIG. 7) to outer surface 26' of electrode 10'. A recessed portion 36 is further provided on outer surface 26'. Recessed portion 36 may be positioned on outer surface 26' of electrode 10' extending from proximal member 42 towards and into distal member 44 of electrode 10'.

FIG. 5A further provides an embodiment with a recessed portion 36 having a substantially constant width. The width of recessed portion 36 may correspond to the diameter of passageway 32 positioned within the recessed portion 36. In particular, the width of recessed portion 36 may correspond to the diameter of, or be substantially the same as, the opening/outlet of passageway 32. An alternate embodiment, such as shown in FIG. 5B, provides a recessed portion 36 having a variable width such that the width of portion 36 tapers as portion 36 extends towards and/or into distal portion 44 of electrode 10'. Electrode 10' may further provide a fluid passageway 32' positioned along the central longitudinal axis (A) of electrode 10'. Fluid passageway 32' provides an outlet/opening on distal end 46 of distal member 44 of electrode 10'.

Figure 6:
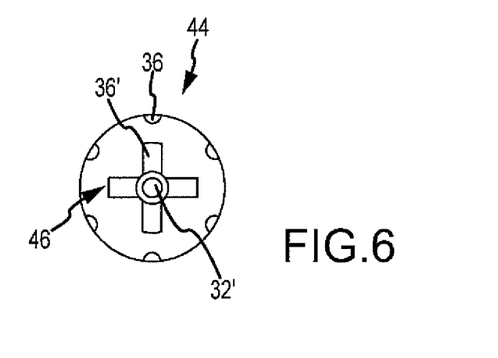
FIG. 6; is a distal end view of the irrigated ablation electrode in an alternate embodiment as shown in FIG. 5A.

An end view in accordance with an embodiment of the present invention, as shown in FIGS. 5A and 5B, is further illustrated in FIG. 6. Distal end 46 includes an opening/outlet for passageway 32' that is positioned along the central longitudinal axis (A) of the electrode 10', as shown in further detail in FIG. 7. Distal end 46 of distal member 44 further includes a plurality of recessed portions 36' positioned about the outlet for passageway 32' on distal end 46 of electrode 10'. As shown in FIG. 6, a particular embodiment provides a cross-like arrangement of recessed portions 36', wherein recessed portions 36' extend from the outlet of passageways 32'. Moreover, recessed portions 36 may be positioned circumferentially about electrode 10' and extend longitudinally along outer surface 26' of electrode 10'. Alternate embodiments may be provided having different recessed portion configurations on distal end 46. The number of recessed portions 36' provided on distal end 46 may vary depending on size and shape of the opening to passageways 32', as well as the intended use of the ablation electrode 10.

FIG. 7 illustrates a cross-sectional view of an embodiment of an ablation electrode 10', such as that provided in FIGS. 5A and 5B. As shown in FIG. 7, ablation electrode 10' is connected to an irrigation catheter assembly 12 including a catheter shaft 30 and a fluid delivery tube 18. Electrode 10' comprises a proximal member 42 and a distal member 44. The proximal member 42 may further be configured to include a portion 56 that extends into distal member 44. The distal member 44 of ablation electrode assembly 10 may have a generally cylindrical shape terminating in a hemispherical end 46. The distal member 44 can be configured to accept portion 56 of proximal member 42 for attachment thereto. The distal member 44 may be connected by any known mechanism including adhesives, press-fit configurations, snap-fit configurations, or any other mechanism known to one of ordinary skill in the art. Proximal member 42 may further include an inner cavity 50 that is connected to fluid delivery tube 18 and acts as a manifold or distributor for transporting and/or distributing fluid to electrode 10'.

Proximal member 42 is comprised of a non-thermally conductive or reduced thermally conductive material that serves to insulate the fluid from the remaining portions of electrode 10'. Moreover, proximal member 42 comprises an electrically nonconductive material. Proximal member 42 is lower in thermal conductivity than distal member 44. In an embodiment, proximal member 42 is made from a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. One reduced thermally conductive material may include polyether ether ketone ("PEEK"). Further examples of reduced thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

The proximal member 42 may be configured to receive a fluid delivery tube 18 carried within catheter assembly 12. Proximal member 42 includes a plurality of passageways 32. Proximal member 42 may serve as a manifold or distributor of fluid to electrode 10' through the use of passageways 32. Passageways 32 extend from inner cavity 50 axially toward the outer surface 26' of electrode 10'. In an embodiment, passageways 32 extend to outer surface 28 of proximal member 42. In an embodiment, a plurality of passageways 32 are substantially equally distributed around proximal member 42 to provide substantially equal distribution of fluid to the targeted tissue area and/or the outside of electrode 10'. Electrode 10' may be configured to provide a single, annular passageway 32, or a number of individual passageways 32 equally distributed around the proximal member 42. Moreover, the passageways 32 may be generally tubular and may have a constant diameter along the length of the passageway. Alternate configurations having various diameters along all or portions of the length of the passageways may be used.

As shown in FIG. 7, a plurality of passageways 32 may extend towards distal member 44 of electrode 10' at an angle ($\Theta$) less than 90 degrees from the central longitudinal axis of electrode 10'. In an embodiment, passageways 32 extends at an angle ($\Theta$) between about 20 to about 70 degrees, and for some embodiments, between about 30 to about 60 degrees. Moreover, passageway 32' extends along the central longitudinal axis of electrode 10' from manifold 50 to distal end 46 of electrode 10'. Passageway 32' may further be fully or partially surrounded by a thermally non-conductive, i.e., insulating, member 52 that prevents a saline or other biocompatible fluid from coming in contact with the portion of electrode 10' provided by distal member 44. Alternate positions and angles of the passageway(s) 32 may be provided in alternate embodiments of electrode 10'.

In operation, fluid is pumped from fluid source 14 through fluid delivery tube 18 and passes into and through inner cavity 50 of proximal member 42. Inner cavity 50 distributes fluid to passageways 32,32' extending to external surface 26' and/or distal end 46, which may include recessed portions 36, 36'. Passageways 32,32' provide outlets positioned in recessed portions 36,36' so that the fluid exits passageways 32,32' into recessed portions 36,36'. The fluid outlet from passageways 32, 32' is transferred along recessed portions 36,36' to the surrounding tissue. Accordingly, the flow of fluid from passageways 36,36' may be improved or maximized even if the outer surface 26' of electrode 10' is in direct contact with the target tissue.

Additional components, such as those known in the art may be integrated and/or incorporated into an electrode 10,10' of the type disclosed by the present invention. Distal member 44 of electrode 10' may further include at least one temperature sensing mechanism 60, such as a thermal sensor, disposed therein for measurement and control of electrode 10'. The temperature sensing mechanism(s) 60 can be any mechanism known to one of skill in the art, including for example, thermocouples or thermistors. The temperature sensing mechanism 60 may further be surrounded, or encapsulated, by a second thermally conductive and electrically non-conductive material 62. This thermally conductive and electrically non-conductive material 62 can serve to hold temperature sensing mechanism 60 in place within distal member 44 and provide improved heat exchange between temperature sensing mechanism 60 and distal member 44. This material may be comprised of a number of materials known to one of ordinary skill in the art, including for example, thermally conductive resins, epoxies, or potting compounds. A power wire 64 may further be provided within distal member 44 of electrode 10'. Both the thermal sensor 60 and power wire 64 extend within the catheter assembly 12, for example, through the proximal member 42 and into distal member 44 of electrode 10.

Figure 8A:
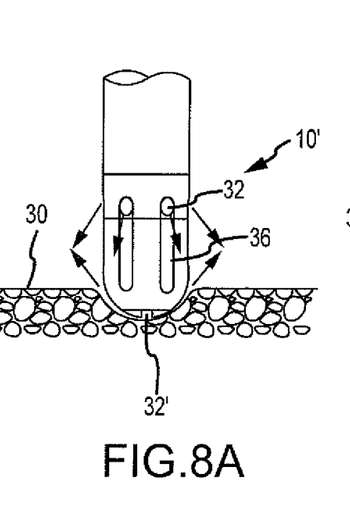
FIGS. 8A and 8B illustrate alternate orientations of an alternate embodiment of an irrigated ablation electrode as shown in FIG. 5A in contact with target tissue.
Figure 8B:
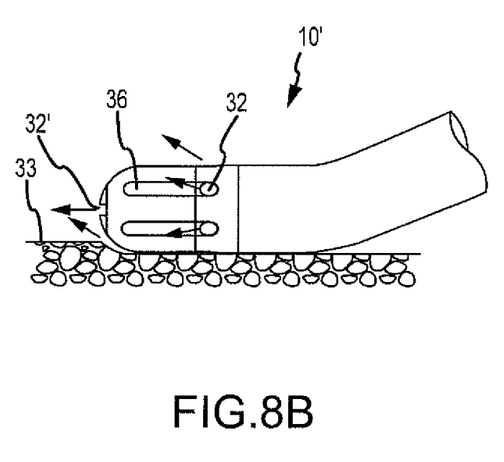

FIGS. 8A and 8B illustrate the fluid flow (as generally demonstrated by the arrows) provided by electrode 10'. FIG. 8A illustrates a perpendicular orientation of electrode 10', wherein distal end 46 of electrode 10' is in direct contact with the target tissue. FIG. 8B illustrates a parallel orientation of an ablation electrode 10', wherein the outer surface 26' of electrode 10', including both the proximal and distal members 42, 44 may be in direct contact with the target tissue. The relative positioning of the outlets of passageways 32 allows the fluid to flow along the surface 26' of electrode 10' within recessed portions 36. Such improved flow of fluid helps prevent passageways 32, in particular the openings/outlets, from clogging during ablation procedures.

Although a number of embodiments of this invention have been described above with a certain degree of particularity, those skilled in the art could make numerous alterations to the disclosed embodiments without departing from the spirit or scope of this invention. Other embodiments and uses of the devices and method of the present invention will be apparent to those skilled in the art from consideration of the specification and practice of the invention disclosed therein.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode for an irrigated ablation catheter comprising: an outer body portion having a proximal portion and distal portion, the outer body portion including an outer surface having at least one first recessed portion, wherein the at least one first recessed portion has a variable width; an inner cavity defined within the outer body portion configured to receive irrigation fluid from a source at a proximal end of the ablation catheter; at least one passageway that extends from the inner cavity to an outlet of the at least one passageway in the at least one first recessed portion and an axial passageway extending along a longitudinal axis of the outer body portion from the inner cavity towards the distal portion and to the outer surface of the outer body portion, the axial passageway having an outlet on an end of the distal portion, wherein the electrode comprises at least one second recessed portion on the outer surface of the end of the distal portion, the at least one second recessed portion extending from the outlet of the axial passageway on the end of the distal portion.

2. The electrode of claim 1, wherein the at least one first recessed portion is disposed circumferentially on the outer surface of the outer body portion.

3. The electrode of claim 1, wherein the at least one first recessed portion includes a plurality of first recessed portions.

4. The electrode of claim 1, wherein the at least one passageway includes a plurality of passageways disposed circumferentially about the outer body portion, and wherein each of the plurality of passageways extends from the inner cavity to the outer surface within the at least one first recessed portion.

5. The electrode of claim 4, wherein the at least one first recessed portion includes a plurality of first recessed portions and wherein the plurality of passageways extend to the plurality of first recessed portions on the outer surface of the body portion.

6. The electrode of claim 1, wherein the at least one first recessed portion has a substantially constant depth.

7. The electrode of claim 1, wherein the at least one first recessed portion has a substantially constant depth and wherein the variable width of the at least one first recessed portion tapers from a first location where the at least one passageway is disposed to a second location further from the at least one passageway.

8. An irrigated ablation electrode for use with an irrigated catheter assembly, the irrigated ablation electrode comprising: an outer body portion including an outer surface, the body portion comprising a proximal member and a distal member including a distal end, the proximal member and distal member being connected, wherein the proximal member includes an inner cavity disposed within the outer body portion configured to receive irrigation fluid from a source at a proximal end of the ablation catheter; at least one passageway extending from the inner cavity to the outer surface of the outer body portion; at least one first recessed portion disposed on the outer surface of the outer body portion, wherein the at least one passageway provides an opening in the at least one first recessed portion and wherein the at least one first recessed portion has a variable width; an axial passageway extending axially along a longitudinal axis of the outer body portion from the inner cavity towards the distal member and to the outer surface of the outer body portion, the axial passageway having an outlet on the distal end of the distal member; wherein the electrode comprises at least one second recessed portion on the outer surface of the distal end of the distal member, the at least one second recessed portion extending from the outlet of the axial passageway on the distal end of the distal member.

9. The irrigated ablation electrode of claim 8, wherein the proximal member is lower in thermal conductivity than the distal member.

10. The irrigated ablation electrode of claim 8, wherein the distal member is comprised of an electrically conductive material.

11. The irrigated ablation electrode of claim 8 wherein the proximal member comprises an electrically nonconductive material.

12. The irrigated ablation electrode of claim 8, wherein the at least one first recessed portion is disposed circumferentially on or about the outer surface of the proximal member.

13. The irrigated ablation electrode of claim 8, wherein the at least one first recessed portion extends from the outer surface provided by the proximal member into the outer surface provided by the distal member.

14. The irrigated ablation electrode of claim 13, wherein the at least one first recessed portion has a substantially constant depth.

15. The irrigated ablation electrode of claim 13, wherein the at least one first recessed portion has a substantially constant depth and wherein the variable width of the at least one first recessed portion tapers from a first location where the at least one passageway is disposed to a second location further from the at least one passageway.

16. The irrigated ablation electrode of claim 13, wherein the at least one passageway includes a plurality of passageways disposed circumferentially about the outer body portion, wherein each of the plurality of passageways extends from the inner cavity to the outer surface of the outer body portion within the at least one first recessed portion.

17. The irrigated ablation electrode of claim 16, wherein the at least one first recessed portion includes a plurality of first recessed portions disposed on the outer surface of the outer body portion and wherein the plurality of passageways extend from the inner cavity to the plurality of first recessed portions on the outer surface of the outer body portion.

18. The irrigated ablation electrode of claim 8, wherein the axial passageway is thermally insulated from the distal member.

* * * * *